United States Patent [19]

Suire et al.

[11] Patent Number: 4,790,851

[45] Date of Patent: Dec. 13, 1988

[54] METHOD FOR MANUFACTURING SURGICAL IMPLANTS AT LEAST PARTIALLY COATED WITH A LAYER OF A METAL COMPOUND, AND IMPLANTS MANUFACTURED ACCORDING TO SAID METHOD

[75] Inventors: René Suire, Montauban De Bretagne; Christian Malet, Paris; Roger J. Speri, Conflans Sainte Honorine; Coll Bernard, Cergy, all of France

[73] Assignees: France Implant; Innovatique S.A., both of France

[21] Appl. No.: 839,404

[22] Filed: Mar. 14, 1986

[51] Int. Cl.⁴ .................. A61F 2/36; C23C 16/00; A01N 1/02
[52] U.S. Cl. .................. 623/16; 623/23; 623/66; 427/255.2; 427/2
[58] Field of Search .................. 623/16, 22, 23, 66; 428/938; 627/2, 38; 427/255.2, 327, 355, 369

[56] References Cited

U.S. PATENT DOCUMENTS

| | | | |
|---|---|---|---|
| 3,577,286 | 5/1971 | Berkenblit et al. | 427/255.2 X |
| 3,643,658 | 2/1972 | Steineman | 623/66 X |
| 3,988,955 | 11/1976 | Engel et al. | 427/38 X |
| 4,136,211 | 1/1979 | Sliney | 427/327 X |
| 4,402,994 | 9/1983 | Kobayashi et al. | 427/38 |
| 4,466,991 | 8/1984 | Andreev et al. | 427/38 |
| 4,587,135 | 5/1986 | Diener et al. | 427/38 X |
| 4,620,913 | 11/1986 | Bergman | 427/38 X |

Primary Examiner—Richard J. Apley
Assistant Examiner—Alan W. Cannon
Attorney, Agent, or Firm—William A. Drucker

[57] ABSTRACT

A method is provided for manufacturing surgical implants at least partially coated with a layer of a metal compound, comprising the formation of an implant blank from a metal or composite substrate having at least one contact bearing surface, a first polishing of this contact bearing surface, cleaning of this contact bearing surface using physico-chemical means, decontamination and heating of this surface by high energy ion bombardment, in a reactor having a structure similar to that of an oven for thermo-chemical treatment by ionic bombardment, the formation of the deposit by creation of metal vapor inside the reactor and by introducing therein a reactive gas.

8 Claims, 1 Drawing Sheet

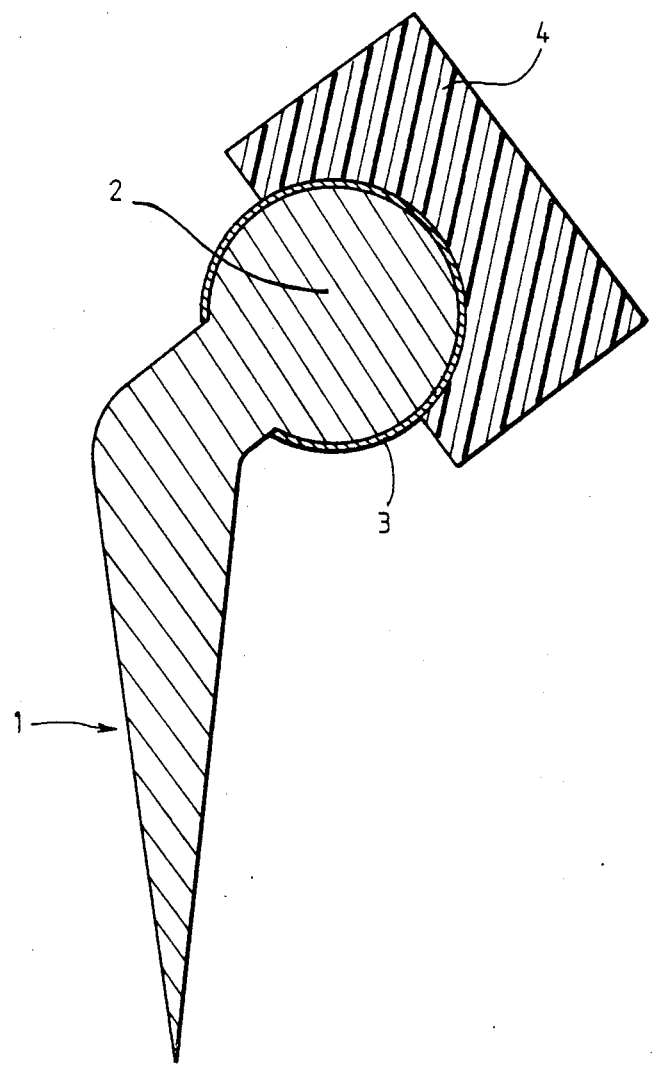

METHOD FOR MANUFACTURING SURGICAL IMPLANTS AT LEAST PARTIALLY COATED WITH A LAYER OF A METAL COMPOUND, AND IMPLANTS MANUFACTURED ACCORDING TO SAID METHOD

BACKGROUND OF THE INVENTION

1. Field of the Invention

The object of the present invention is a method for manufacturing surgical implants to be used in particular but not exclusively, for manufacturing internal articular prostheses. It also concerns an implant constructed according to said method.

2. Description of the Prior Art

It is generally known that the construction of internal prostheses gives rise to numerous problems, in particular a problem of biocompatibility with the surrounding living tissues and problems connected with the chemical and/or mechanical interactions of the prosthesis with said tissues or even between two distinct parts of the prosthesis.

These problems arise in a particular keen way for articular prostheses which are often subjected to considerable mechanical constraints while having to carry out a complex articulation function.

Thus, for this type of prostheses, there are further problems relating to the surfaces of contact of the different parts of the articulation which undergo relative displacements and are thus subjected to frictions.

It is clear that these contact surfaces, by which the articulation function is re-established and on which the transmission of forces takes place must have a very high precision, be smooth and hard, and have a very low friction coefficient, and more particularly a very low index of roughness.

This is why numerous researches have been carried out up to now for finding a material having all the properties required for resolving the above mentioned problems. Thus, in the field of highly resistant materials, metals or metal compounds have been proposed such as cobalt, chromium, molybdenum alloys or stainless steel. However, it has proved that these materials have a certain number of disadvantages, more particularly in so far as their weight is concerned (density which is much greater than that of bone (8 to 10 times greater)) and shaping thereof. Another disadvantage of stainless steels comes from the fact that in them the chromium which is present in these stainless steels and which serves as protection agent against corrosion disappears in the presence of chlorine ions therefore, the prosthesis which is subjected to the action of the chlorine ions present in the surrounding living tissues, will be no longer protected against corrosion and will finish by breaking whatever its weight and its volume.

Implants made of carbon/resin composites have been also tested. However, these composites have been rejected becaue of the toxicity of the resin used up to now.

Because of this toxicity researches have then turned towards the production of a carbon-carbon composite whose advantages may be briefly resumed as:
- a priori perfect biocompatibility,
- density very close to that of the cortical bone,
- the possibility of obtaining a heterogeneous structure,
- elasticity very close also that of the boney cortical substance,
- biochemical and electrochemical inertia.

However, it has proved that this material does not provide contact surfaces having the required properties, more particularly in so far as the hardness and resistance to abrasion are concerned.

This is why attempts have been made to carry out treatments on these contact bearing surfaces for obtaining sufficiently smooth and hard surface conditions. However, the results of friction tests carried out on contact bearing surfaces treated with conventional methods, more particularly by deposition of titanium nitride according to the methods of the CVD ("Chemical Vapor Deposition") type have not been thought sufficient and the use of this composite material has been temporarily rejected and similar tests have been carried out on implants made from titanium alloy, in particular TA 6 V which comprises 90% titanium, 6% aluminium and 4% vanadium.

In this case also, the problem of treating the contact bearing surfaces is just as keen with in addition the problems relative to the deformations undergone by the metal at the treatment temperatures (usually high), these deformations of course leading to inadmissable defects of precision of the implant, once treated.

The invention overcomes these problems.

SUMMARY OF THE INVENTION

It provides a manufacturing method based on the numerous teachings of tests previously mentioned and which allows contact bearing surfaces to be obtained coated with an inert, chemically stable and biocompatible metal compound such as a carbide or nitride having the required mechanical properties. According to the invention, this process comprises more particularly the following operations:

- the formation of an implant blank in a metal or composite substrate comprising at least one contact bearing surface substantially to the dimensional tolerances of those of the finished product;
- a first polishing of this contact surface;
- preparation of the surface of this contact portion once polished, this preparation consisting in cleaning with physico-chemical means;
- a first treatment phase comprising decontamination of this surface by bombardment with high energy ions coming from an evaporation source, the first treatment phase being carried out in a reactor having a structure similar to that of a thermochemical treatment oven with ionic bombardment in a treatment atmosphere comprising a rare gas such as argon or nitrogen at a pressure of $10^{-6}T$ to a few millitorrs, the pieces subjected to this treatment being brought to a cathode potential higher than 800 volts so as to repulverise the incident ions;
- heating of the implant to a predetermined temperature compatible with that at which said deposition is to be carried out, this heating being at least partially provided solely by transformation of the kinetic energy of the ions into heat energy;
- once said temperature has been reached, the formation of said deposition by creation of metal vapor inside the reactor, by introducing into the reactor a reactive gas and by reducing the cathode potential of the implant to a value which may be between 100 and 400 volts;
- final polishing of the surface of the bearing portion comprising said deposition.

It is clear that in this process, the desired result can only be obtained to the extent that each of the above mentioned operating phases is suitably carried out.

Thus, the formation of the blank and the first polishing must necessarily lead to obtaining contact bearing surfaces having a high precision form (tolerance at most or equal to 10 microns for the sphericity) and a surface having an index of roughness equal at most to 0.10 micron, this result being able to be obtained more particularly by evolutive grinding with abrasive paste.

The purpose of the phase for preparing the surface of the bearing portion is to remove all the surface pollution likely to contaminate the piece and consequently, to adversely affect the quality of the subsequent deposition, such pollution coming more particularly from the products used for manufacturing the blank and during the first polishing, from oxidization of the piece or even from impurities deposited on the piece (for example dust) which may come from various pollution sources.

Such preparation must preferably be carried out in a non oxidizing atmosphere, more particularly because of the fact that some metals forming the substrate are very rapidly oxidized. Similarly, it will be suitable to use products inert with respect to the substrate and this, so as to avoid any possibility of corrosion. Thus, in the case of a titanium based substrate, the use of chlorinated agents will be avoided.

Such preparation may more particularly comprise microsanding, ultrasonic cleaning, alkaline cleaning, rinsing and vapor phase drying. An antistatic agent such for example as an antistatic "freon" may further be used for avoiding any subsequent dust deposit.

The purpose of the first treatment phase is to eliminate by ionic cleaning on the atomic scale any trace of oxidization on the surface of the substrate. Preferably, this first treatment phase is carried out in a reactor which will subsequently be used for effecting the deposition of the surface layer and which necessarily comprises a sealed enclosure inside which the pieces to be treated may be disposed, an anode which may be formed by the wall of the enclosure, means for bringing the piece to be treated to a cathode potential, and means for obtaining metal vapor.

This first treatment phase is obtained through ionic bombardment using heavy ions such as titanium ions or hafnium ions, by providing between the cathode and the anode a high electric voltage of the order of 1000 volts or more, the structure of the reactor and more particularly the anode/cathode distance being provided so that the current remains at a level lower than the threshold from which arc conditions occur for example of the order of 10 to 30 amps.

Thus, ionic bombardment is obtained in which the high kinetic energy ions strike the surface to be treated while being repulverized. During these impacts, a fraction of this kinetic energy is transformed into heat energy causing heating of the piece.

Advantageously, this first treatment phase will be continued until the piece is brought to the temperature at which the metal deposition is to be effected.

Of course, this temperature depends on the nature of the substrate to be used, on the nature of the deposition and on the method used for effecting this deposition. As mentioned above, it will remain less than a temperature threshold beyond which the piece to be treated risks undergoing deformations incompatible with the required precision. Thus, for the whole of the materials which may be used for the substrate, it has proved that this temperature should not exceed 750° C. and should remain less than 450° C., in the particular case of depositing titanium nitride on a titanium or titanium alloy substrate.

The metal deposition is then carried out by using means for obtaining a metal vapor with, concurrently, the injection inside the reactor of treatment gases. These gases may comprise nitrogen, in the case where the deposition which it is desired to effect is a nitride, oxygen for obtaining an oxide or a hydrocarbon for obtaining a carbide.

During this treatment phase, the cathode potential of the piece to be treated is lowered to a voltage which may be between 100 and 400 volts.

The growth kinetics of the layer deposited on the substrate depends on numerous parameters such as the nature of the means for evaporating the metal, their number, their arrangement, their distance to the piece. However, in practice, for a given reactor and a given piece, the thickness of the layer may be defined by the treatment time.

The means for obtaining the metal vapor usable in the method of the invention may be of two types, namely:
 a first type in which the metal vapor is obtained by thermal evaporation for example by Joule effect, by induction, by laser radiation, by means of an electron beam gun, or a hollow cathode gun or even using electric arcs;
 a second type in which the metal vapor is obtained by cathode spraying, in a diode, triode, magnetron or ion beam gun type circuit.

Excellent results have been obtained with a reactor using, for obtaining the metal vapors, the principle of the formation of electric arcs self sustained on a target placed above the piece to be treated and cooperating with a moble electrode brought to a potential of the order of 20 to 40 volts with respect to the target by means of a power supply circuit delivering a current of the order of 50 amps, and which may reach 100 amps.

Positioning of the pieces inside the reactor was then provided by planetary arrangement allowing perfect adjustment of the orientation of the surfaces to be treated of the piece with respect to the target and guaranteeing thus the homogeneity of the coating formed on these surfaces.

In tests carried out under these conditions on titanium alloy (TA 6 V) work pieces, an extremely adherent and hard (of the order of 3000 HV) titanium nitride coating was obtained and this for very small thicknesses (of the order of 1 to 5 microns). After final polishing, roughness indices less than or equal to 0.050 micron were obtained.

One example of forming an implant in accordance with the process of the invention is shown in the single FIGURE of the accompanying drawing.

The implant 1 shown in this FIGURE is of the type used in a hip prosthesis. It comprises a contact bearing surface 2 in the form of a spherical ball joint coated with a layer 3 obtained using the above described method.

Mechanical tests were carried out more precisely on implants of this kind formed of a titanium alloy substrate (TA 6 V) and a titanium nitride layer.

The purpose of these tests was to assess the value of the friction torque of the contact surfaces on a high density polyethylene 4 cotyl and this under unduly severe operating conditions (optimized bending moment, load of 300 kg), the whole being plunged in an aggressive medium and causing the two parts to swivel at a frequency of 1 Hz to one million cycles. During these tests, different parameters were measured, more particularly the sphericity of the ball joints, the heat release obtained and the value of the wear of the different components under friction.

These tests showed that the best results were obtained in the case of contact bearing surfaces having coatings of small thickness (less than 5 microns and in particular of the order of 1 micron after final polishing).

In fact, in this case, the disadvantages of thick layers are avoided and more particularly the problems of decoherence of the deposit under the effect of tangential stresses produced by friction, as well as the problems of cracking of the coating due to the thermal stresses undergone by the piece during treatment.

Of course, the invention concerns the implants obtained using the above described method and more particularly implants at least partially coated with a layer formed of a metal compound having a thickness less than 25 microns and, preferably, of the order of 1 micron.

These implants may advantageously comprise a titanium alloy substrate, for example made from "TA 6 V" and a titanium nitride layer.

However, the invention is not limited to such an association.

Thus, the implant blank may for example be formed by machining a block of a carbon/carbon composite obtained by densification of carbon fibers by chemical deposition in the fluid phase of a pyrocarbon matrix. Generally, chemical deposition of the pyrocarbon matrix is carried out in the vapor phase. The carbon fibers are organized in the form of a carbon fabric stack obtained by carbonization of fibers of a carbonated polymer for example polyacrylonitrile.

For obtaining a three dimensional isotrope structure, the carbon fabric stacks are stacked perpendicularly to the mean plane defined by this stack by other carbon fibers which thus create a three dimensional structure.

This type of product is commercialized by the firm GV Systems, 33 rue Rameau, 94800 Villejuif, France, under the name "carbon/carbon composite" in different qualities corresponding to voluminal masses which may vary between 1.2 and 2. It has proved that these voluminal masses were very suitable and, because they are close to the bone density, inertial effects caused by the implant are avoided when the implant is made from a dense material such as stainless steel. Furthermore, it has been discovered that the elasticity of this material was very close to the boney cortical substance.

Similarly, the invention is not limited to the use of a titanium nitride layer. In fact, this layer could also consist of a compound chosen from:

titanium carbide,
titanium oxide,
silicon carbide,
silicon nitride,
aluminium oxide,
molybdenum bisulphide,
hafnium nitride.

The main advantages of this type of coating in the field of surgical implants have been mentioned above. However, it should be further noted that these different products, in particular titanium nitride, are perfectly wettable products, that is to say that in vivo the titanium nitride coated surfaces are continually lubricated by the biological fluids, so that a reduction of the wear of the surfaces by friction is obtained.

It has also been noted that, unlike surgical implants made from a metal material which tend to take on static charges, the substrate/titanium nitride layer association does not tend to be charged electrically. This is very important for the influence of static charges has been shown on necroses under surgical implants as well as poor reformations of the callus because of the presence of an electrostatic charge.

Moreover, the influence has been shown of the porosity of the substrate on the quality of the coating obtained. Thus, in the case of a carbon/carbon composite, it has proved preferable to use a block of this composite having a mean pore diameter less than 10 microns and, preferably, less than 5 microns.

Considering the technology used, it has proved preferable, when the deposition of the product such as titanium nitride is to be effected in the vapor phase, to effect the vapor phase deposition over the whole of the surgical implant and to remove this coating at the places where it is not desired for biocompatibility reasons.

Thus, in the case of a hip prosthesis, only the prosthesis head requires a titanium nitride coating, whereas, on the contrary, the lower part must be made from carbon so as to ensure maximum biocompatibility when it is inserted in the top of the femur.

It is also possible to provide for the two contacting surfaces to be coated, thus, in the case of a hip prosthesis, coating of the cotyl may also be provided.

Other prostheses may of course be considered which could benefit from such a coating. It is a question for example of total knee prostheses, articular tarsometatarsus prostheses, for example at the level of the first metatarsus; or else, it may be a question of wrist prostheses with as secondary aim the total replacement of the following bone parts:

semilunar,
scaphoid.

Tests carried out up to now have shown that, for example in the case of an animal hip prosthesis formed of a porous carbon/carbon base (porosity of about 80%) comprising a femur head coated with a titanium nitride layer, extremely low friction torques were obtained with respect to currently used materials.

We claim:

1. A method of manufacturing surgical implants comprising a substrate at least partially coated with a deposition formed of a metal compound, comprising the following steps:
 i. a step of forming an implant blank from an electrically conductive substrate, said blank comprising at least one contact bearing surface having dimensional tolerances substantially equal to those of the finished implant;
 ii. a step of initial polishing of this contact bearing surface;
 iii. a step of cleaning of the contact bearing surface, once polished, by physico-chemical means;
 iv. a step of decontaminating by an ionic cleaning on the atomic scale of any trace of oxidisation of this contact bearing surface, said decontaminating step being carried out by bombarding this surface with heavy ions such as titanium ions and hafnium ions coming from an evaporation source, in a reactor having a structure similar to that of an oven for thermo-chemical treatment by ionic bombardment in a non oxidizing atmosphere comprising a neutral gas such as argon or nitrogen, at a pressure of $10^{-6}$T to a few millitors, the implant blank being brought to a cathode potential greater than 800 volts so as to obtain an ionic bombardment of the contact bearing surface in which high kinetic energy ions strike the contact bearing surface while being repulverized and a fraction of the kinetic energy of the ions is transformed into heat energy causing heating of the blank;

v. a step of heating of the blank to a predetermined temperature at which said deposition is to be carried out, such heating being at least partially obtained in the decontaminating step by the transformation of the kinetic energy of the ions;

vi. once said predetermined temperature has been reached, the formation of said deposition by creating metal vapor inside the reactor, by introducing into the reactor a reactive gas and by reducing the cathode potential of the blank to a value between 100 and 400 volts;

vii. a step of final polishing of the contact bearing surface comprising said deposition.

2. The method as claimed in claim 1, wherein said steps of initial polishing of the bearing contact surface is carried out until the index of roughness of said bearing contact surface has reached 0.10 micron.

3. The method as claimed in claim 1, wherein said step of decontaminating comprises at least one of the following treatments, a microsanding treatment, an ultrasonic cleaning treatment, an alkaline cleaning treatment, a rinsing treatment, a vapor phase drying treatment and an application of an antistatic agent.

4. The method according to claim 1, wherein the ionic bombardment effected in the step of decontaminating the contact bearing surface is effected by using a cathode potential greater than 1000 volts with a cathode/anode current maintained below a threshold from which arcing conditions occur.

5. The method as claimed in claim 1, wherein said substrate is made from a titanium alloy, the metal vapor is titanium vapor, and the reactive gas comprises nitrogen so as to obtain on the substrate a layer of titanium nitride.

6. The method as claimed in claim 1, wherein the temperature at which the deposition is effected is less than 750° C. and less than 450° C. in the case of a titanium alloy substrate.

7. The method as claimed in claim 1, wherein the metal vapor used for forming the deposit is obtained by forming self sustained electric arcs on a metal target disposed inside the reactor.

8. The method as claimed in claim 1, wherein the duration of the deposition phase is determined so as to obtain a deposit having a thickness less than 25 microns and, preferably, less than 5 microns.

* * * * *